(12) United States Patent
Tanaka et al.

(10) Patent No.: US 6,362,005 B1
(45) Date of Patent: Mar. 26, 2002

(54) NITROGEN DIOXIDE GAS SENSING METHOD, NITROGEN DIOXIDE GAS SENSOR ELEMENT, AND NITROGEN DIOXIDE GAS SENSOR USING THE SAME

(75) Inventors: Tohru Tanaka; Takayoshi Hayashi; Shiro Matsumoto; Yasuko Maruo; Takashi Ohyama, all of Tokyo (JP)

(73) Assignee: Nippon Telegraph and Telephone Corporation, Tokyo (JP)

( * ) Notice: Subject to any disclaimer, the term of this patent is extended or adjusted under 35 U.S.C. 154(b) by 0 days.

(21) Appl. No.: 09/139,066

(22) Filed: Aug. 24, 1998

(30) Foreign Application Priority Data

Aug. 29, 1997 (JP) ............................. 9-234193
Jun. 30, 1998 (JP) ............................ 10-184507

(51) Int. Cl.⁷ .................. G01N 33/00; G01N 21/01; G01N 21/25; G01N 31/22
(52) U.S. Cl. .............. 436/117; 422/56; 422/57; 422/82.09; 422/86; 422/87; 422/88; 422/91; 436/118; 436/169
(58) Field of Search ................. 436/117, 116, 436/118, 169; 422/82.09, 91, 57, 56, 86–88

(56) References Cited

U.S. PATENT DOCUMENTS

| | | | | |
|---|---|---|---|---|
| 2,963,351 A | * | 12/1960 | Stanford et al. | 422/86 |
| 3,512,937 A | * | 5/1970 | Schulze | |
| 3,681,027 A | * | 8/1972 | Smith | 422/55 |
| 3,817,705 A | * | 6/1974 | Stein et al. | |
| 4,907,037 A | * | 3/1990 | Boisde et al. | 356/412 |
| 4,913,881 A | * | 4/1990 | Evers | 356/402 |
| 5,063,164 A | * | 11/1991 | Goldstein | 422/56 |
| 5,573,953 A | * | 11/1996 | Marnie et al. | 422/82.05 |
| 5,618,493 A | * | 4/1997 | Goldstein et al. | 422/82.05 |

FOREIGN PATENT DOCUMENTS

| | | |
|---|---|---|
| EP | 214768 | 3/1987 |
| JP | 55-103460 | 8/1980 |
| JP | 5-341433 | 12/1993 |
| JP | 6-300685 | 10/1994 |
| JP | 09274032 | 10/1997 |
| JP | 9-274032 | 10/1997 |
| WO | WO8805911 | 8/1988 |
| WO | WO96/14573 | 5/1996 |

OTHER PUBLICATIONS

B. Dimitriades Health Lab. Sci. 1975, 12, 259–266, Jul. 1975.*
M. Tabacco et al. SPIE 1992, 1587, 271–277.*
Database WPI, Section Ch, Week 8807, Derwent Publications Ltd., London, GB, XP–002093597 and JP 63001970.
Database WPI, Section Ch, Week 8510, Derwent Publications Ltd., London, GB, XP002093598 and JP 60012999.
Punkkinen R K: "Automatic colorimetric detector for traces of nitrogen dioxide in air" Review of Scientific Instruments, vol. 59, No. 1, Jan. 1988 pp. 163–16.

* cited by examiner

Primary Examiner—Arlen Soderquist
(74) Attorney, Agent, or Firm—Blakey Sokoloff Taylor & Zafman

(57) ABSTRACT

In this invention, a mixture of a diazotizing reagent which reacts with nitrous ions to produce a diazo compound, a coupling reagent which couples with a diazo compound to produce an azo dye, and an acid is placed in pores of a transparent porous body to prepare a sensor element. Nitrogen dioxide gas is sensed in accordance with a color change before and after the sensor element is exposed to air to be measured for a predetermined time.

13 Claims, 6 Drawing Sheets

ABSORBANCE = $LOG_{10}(I_0/I)$

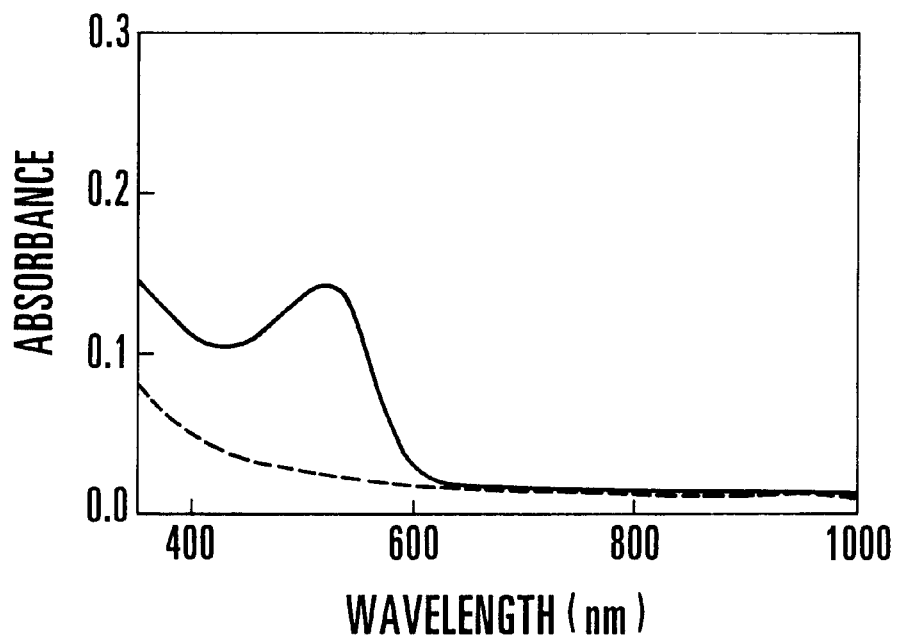
F I G. 6
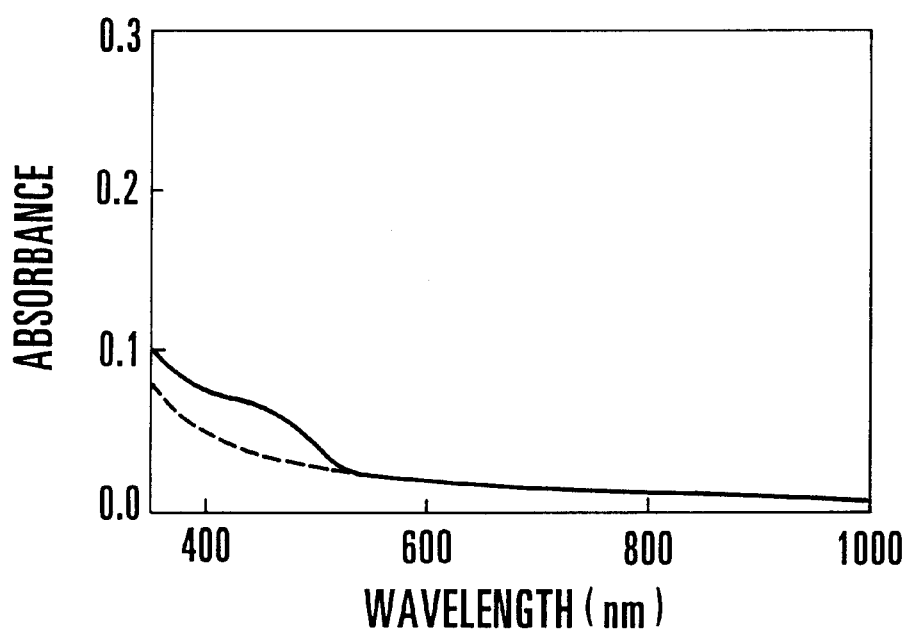
F I G. 7

NITROGEN DIOXIDE GAS SENSING METHOD, NITROGEN DIOXIDE GAS SENSOR ELEMENT, AND NITROGEN DIOXIDE GAS SENSOR USING THE SAME

BACKGROUND OF THE INVENTION

The present invention relates to a nitrogen dioxide gas sensing method, a nitrogen dioxide gas sensor element, and a nitrogen dioxide gas sensor using the same.

Currently, the influence of $SO_2$ and $NO_x$ on the environment poses a problem. $SO_2$ and $NO_x$ are produced by combustion of fossil fuels and cause acid rain and photochemical smog. In Japan, environmental standards are set for these pollutants, e.g., the concentration of atmospheric $NO_2$. Gas concentration measurement is performed by an automatic measurement method in regular monitoring stations at different locations. As an environmental standard, the average value per hour in a day is approximately 60 ppb or less.

Although these gas concentration meters can measure a few ppb, i.e., a slight amount of gas, they are expensive and require maintenance. Also, automatic measurement requires an enormous cost for electricity and the like, and a power supply and an installation place must be secured for the measurement. However, to accurately investigate gas concentration distributions and evaluate terrestrial environmental influence, it is necessary to increase the number of monitoring locations and perform nationwide environmental monitoring. For this purpose, the cumulative use of inexpensive, small, and easy-to-use gas sensors or simple measurement methods (or monitoring devices) is possible.

Presently, the development of a semiconductor gas sensor, a solid-electrolyte gas sensor, an electrochemical gas sensor, and a quartz oscillation gas sensor is being extensively made. However, these sensors are developed to evaluate response in a short time period; i.e., only few sensors are developed for monitoring requiring data accumulation. Also, since the sensitivity is about 1 ppm, these sensors cannot sense real environmental concentrations (e.g., about 10 ppb for $NO_x$). Additionally, the influence of other gases is not negligible in many instances.

A method using a sensor tube gas meter is also developed to perform short-time measurement on the spot but is difficult to use in cumulative measurement. Furthermore, an operator must go to the measurement site, and personal errors occur in reading colors. In many instances, interference of other gases or disturbance is a problem.

A common simple measurement method is to receive air by using a pump, collect $NO_x$ gas by directly collecting it into a sampling bag (a direct collection method), by using a solid-state adsorbent (a solid collection method), or by collecting it into an absorbing solution (a liquid collection method), and analyze the collected gas by gas chromatography. In any of these methods, however, it is necessary to transport not only samples but also peripheral apparatuses such as a pump. In the direct collection method, it is difficult to store gas because the size of the sampling bag is limited. The solid collection method and the liquid collection method require a process of sensing the collected gas.

As a simple monitoring method requiring no suction, the use of a passive sampler for environmental measurement has attracted attention. Examples of an $NO_x$ passive sampler are a nitration plate method and a triethanolamine (TEA) batch method. The effects of the wind speed, temperature, and humidity are examined to examine the quantitativeness. A general approach of measurement after sampling is to clean the sample to form a solution and analyze the solution by ion chromatography or absorptiometric analysis. Unfortunately, these samplers require cumbersome processes such as cleaning after collection and before analysis.

As a method of solving these problems, an $NO_x$ gas sensing method has been proposed. In this method, $NO_2$ gas is reacted with a sensing reagent adsorbed in pores of a porous body as a transparent matrix adsorbent, and the transmitted UV-visible absorption spectrum is measured by a spectrophotometer to sense the amount of $NO_2$. However, a side reaction occurs in this sensing method because a highly reactive material is used as the sensing reagent. Consequently, the sensitivity of the reaction product with $NO_2$ as a target substance does not increase in the UV-visible absorption spectrum. Additionally, the side reaction product disturbs the UV-visible absorption spectrum to make high accuracy impossible to obtain.

In fine, the conventional methods require large expensive apparatuses to accurately sense nitrogen dioxide gas of the order of ppb in accordance with the environmental standards. Also, these methods are too cumbersome to allow easy detection of nitrogen dioxide gas.

SUMMARY OF THE INVENTION

It is, therefore, a principal object of the present invention to simply and accurately sense nitrogen dioxide gas.

To achieve the above object, according to an aspect of the present invention, a mixture of a diazotizing reagent which reacts with nitrous ions to produce a diazo compound, a coupling reagent which couples with the diazo compound to produce an azo dye, and an acid is placed in pores of a transparent porous body to prepare a sensor element. The light transmittance of this sensor element is measured to calculate the first transmittance. The sensor element is then exposed to air to be measured for a predetermined time. After that, the light transmittance of the sensor element is measured to calculate the second transmittance. Nitrogen dioxide gas in the air to be measured is sensed in accordance with the difference between the first and second transmittances.

In this method with the above arrangement, when the sensor element is exposed to an atmosphere containing nitrogen dioxide gas, the diazotizing reagent diazotizes nitrous ions produced by nitrogen dioxide adsorbed to pores of the sensor element to produce a diazo compound. The coupling reagent couples with this diazo compound to produce an azo dye. Consequently, the sensor element colors to make a difference between the first and second transmittances. This allows detection of the nitrogen dioxide gas.

According to another aspect of the present invention, a nitrogen dioxide gas sensor element comprises a transparent porous body, a diazotizing reagent placed in pores of the porous body to react with nitrous ions to produce a diazo compound, a coupling reagent placed together with the diazotizing reagent in the pores of the porous body to couple with a diazo compound to produce an azo dye, and an acid placed together with the diazotizing reagent in the pores of the porous body.

When nitrogen dioxide gas enters the pores of the nitrogen dioxide gas sensor element with the above arrangement and is adsorbed to the pores, the diazotizing reagent reacts with nitrous ions produced by the nitrogen dioxide gas to produce a diazo compound. The coupling reagent couples with this diazo compound to produce an azo dye. Consequently, the nitrogen dioxide gas sensor element colors.

According to still another aspect of the present invention, a nitrogen dioxide gas sensor comprises a light-emitting unit for emitting light, a light-sensing unit having a light-receiving surface opposed to a light-emitting surface of the light-emitting unit to output an electrical signal corresponding to a light amount received by the light-receiving surface, a sensor element inserted between the light-emitting unit and the light-sensing unit, and an electric meter for measuring the state of the output electrical signal from the light-sensing unit. The sensor element comprises a transparent porous body, a diazotizing reagent placed in pores of the porous body to react with nitrous ions to produce a diazo compound, a coupling reagent placed together with the diazotizing reagent in the pores of the porous body to couple with the diazo compound to produce an azo dye, and an acid placed together with the diazotizing reagent in the pores of the porous body.

In the sensor with the above arrangement, when nitrogen dioxide gas enters the pores of the sensor element and is adsorbed to the pores, the diazotizing reagent reacts with nitrous ions produced by the nitrogen dioxide gas to produce a diazo compound. The coupling reagent couples with this diazo compound to produce an azo dye. Consequently, the nitrogen dioxide gas sensor element colors. Meanwhile, the light emitted from the light-emitting unit enters the light-sensing unit via the sensor element. The electric meter measures the color change of the sensor element as a change in the output electrical signal from the light-sensing unit.

BRIEF DESCRIPTION OF THE DRAWINGS

FIG. 6 is a graph showing the results of detection according to the second embodiment of the present invention;

FIG. 7 is a graph showing the results of detection according to the third embodiment of the present invention;

DESCRIPTION OF THE PREFERRED EMBODIMENTS

Figure 1A:
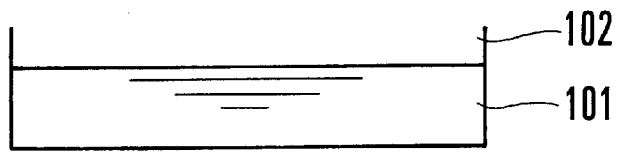
FIGS. 1A to 1F are views for explaining a nitrogen dioxide ($NO_2$) gas sensing method according to the first embodiment of the present invention.

Embodiments of the present invention will be described in detail below with reference to the accompanying drawings.
First Embodiment A nitrogen dioxide ($NO_2$) gas sensing method according to the first embodiment of the present invention will be described below. First, a method of manufacturing a nitrogen dioxide gas sensor element will be described. As shown in FIG. 1A, sulfanilic acid (SA) as an aromatic amine serving as a diazotizing reagent and N,N-dimethylnaphthylamine (DMNA) as a coupling reagent were dissolved in a mixture solution of water and ethanol to prepare a sensing reagent solution 101 in a vessel 102. The concentration of sulfanilic acid was 0.02 mol/l.

Figure 1B:
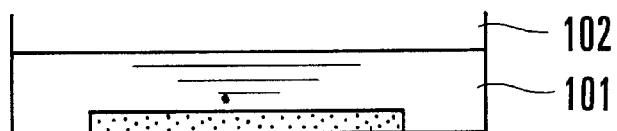

Next, as shown in FIG. 1B, a porous body 103 as porous glass having an average pore-diameter of 4 nm was immersed in this sensing reagent solution 101. VYCOR®7930 manufactured by Corning Glass Works was used as this porous body 103. The average pore-size of this VYCOR®7930 was 4 nm. The chip dimensions of the porous body 103 were 8 (mm)×8 (mm) and a thickness of 1 (mm).

VYCOR®7930 was borosilicate glass. An alkali component and other components mainly consisting of silicon were separated by heating. In this state, an acid treatment was performed to elute the alkali component and form a porous body. Since the acid treatment was performed during the course of manufacture, pores of VYCOR®7930 had an acidic environment. That is, an acid previously existed. If the pores of the porous body are not acidic, acid cleaning or the like is previously performed to make an acid present as an acidic environment in the pores. The porous body in this state need only have, e.g., pH 1.

As a transparent porous body, a porous body made from an organic polymer can also be used.

Figure 1C:
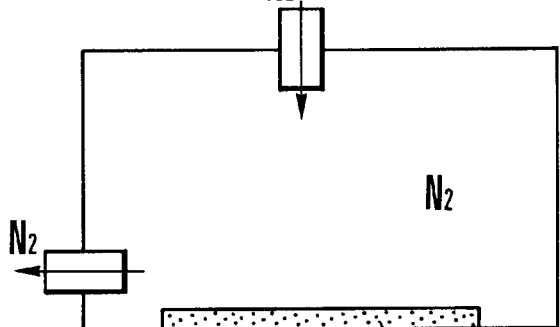

The porous body 103 as described above was immersed in the sensing reagent solution 101 for two hours. After the pores of the porous body 103 were impregnated with the sensing reagent solution, the porous body 103 was air-dried. Finally, as shown in FIG. 1C, the porous body 103 was dried by leaving it in a nitrogen gas flow for a half day to manufacture a sensor element 103a. Although the sensor element is a plate-like element in the above embodiment, a fiber-like element is also usable.

Figure 1D:
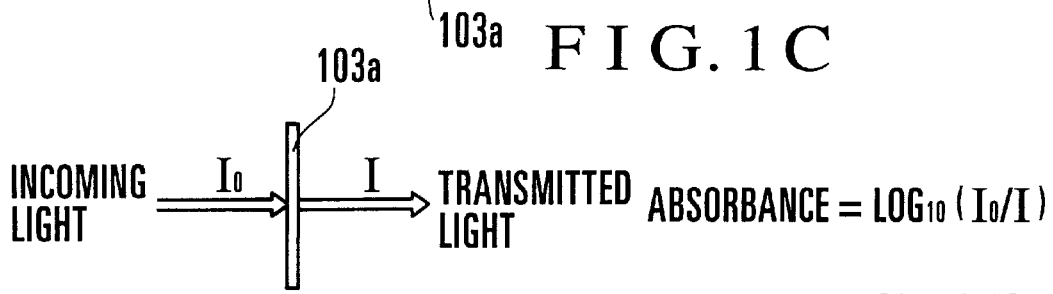

A nitrogen dioxide gas sensing method using the sensor element 103a will be described below. First, as shown in FIG. 1D, the absorbance in the direction of thickness of this sensor element 103a was measured. In FIG. 1D, reference symbol $I_0$ denotes incoming signal light intensity; and I, transmitted light intensity.

Figure 1E:
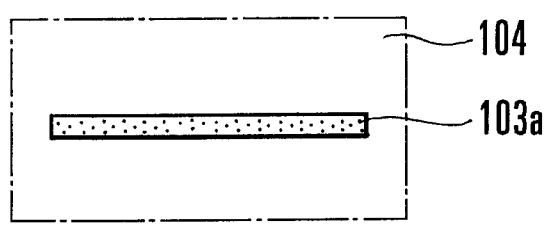

Next, as shown in FIG. 1E, the sensor element 103a was exposed for three hours to air 104 as an object to be sensed in which 300-ppb nitrogen dioxide existed.

Figure 1F:
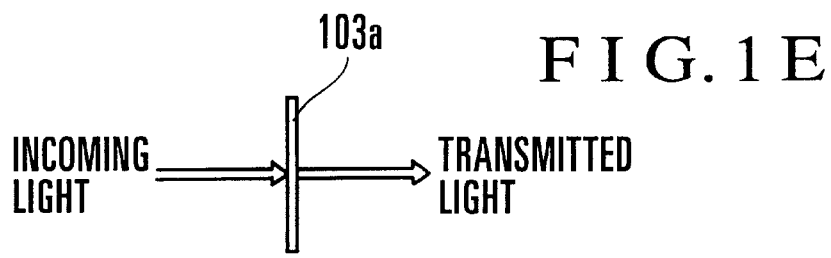

The sensor element 103a was extracted from the air 104, and, as shown in FIG. 1F, the absorbance in the thickness direction of the sensor element 103a was again measured.

Figure 2:
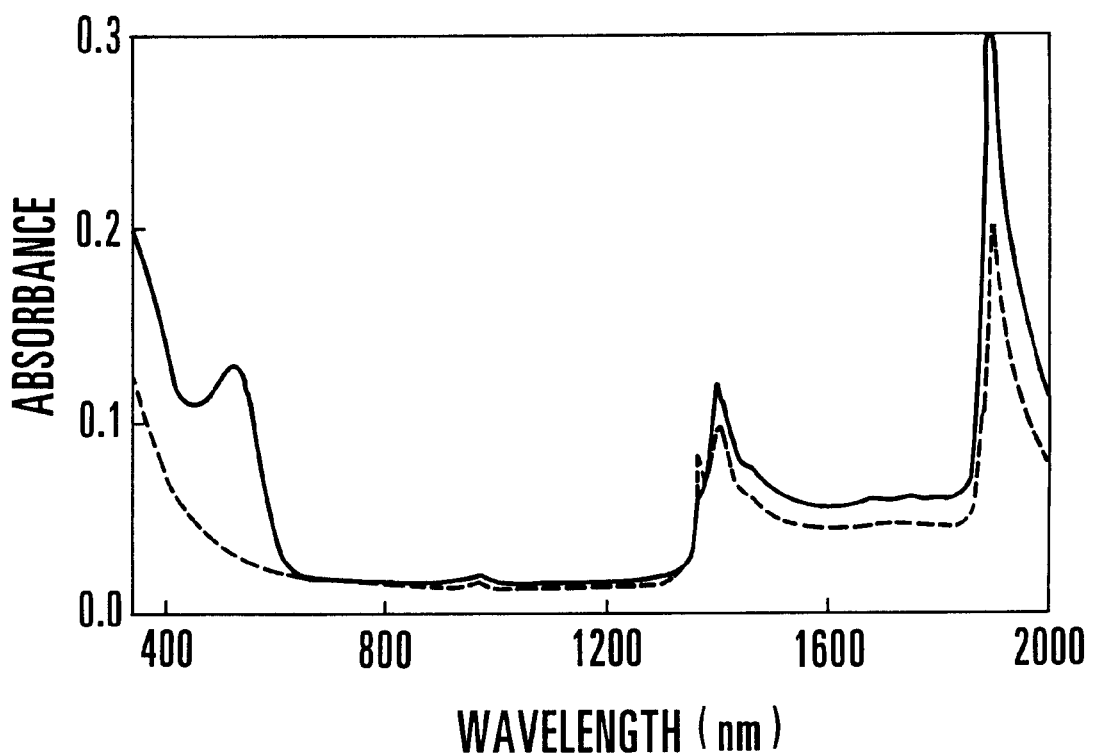
FIG. 2 is a graph showing the results of two absorbance measurements done by the sensing method of the first embodiment.

FIG. 2 shows the results of these two absorbance measurements. No measurements were performed at a transmitted light measurement wavelength of 350 nm or less because the porous glass (VYCOR®7930) forming the sensor element adsorbed the wavelength. Referring to FIG. 2, the absorbance measurement result before the sensor element was exposed to the air to be sensed is indicated by the broken line, and the absorbance measurement result after the element was exposed is indicated by the solid line.

Both of the solid and broken lines have absorption considered as absorption by water near 1,350 and 1,900 nm, respectively. This absorption changed with the humidity of the air to be sensed and the time during which the sensor element was left to stand. Therefore, in this nitrogen dioxide gas sensing method using the sensor element of the first embodiment, it is determined that the effective measurement wavelength range is 350 to 1,000 nm.

A large difference is found between the solid and broken lines at 400 to 600 nm, especially near 530 nm. That is, absorption appeared near 530 nm in the absorbance measurement after the sensor element was exposed to the air to be sensed. This means that a new substance having light absorption at 530 nm was produced in the sensor element when the element was exposed to the air to be sensed. This substance can be presumed to be an azo dye produced when N,N-dimethylnaphthylamine coupled with a diazo compound produced by the reaction between the sulfanilic acid and the nitrous ions. Nitrogen dioxide is dissolved in water to become nitrous ions. Also, since only one absorption peak newly appeared, no other side reactions took place.

Figure 3A:
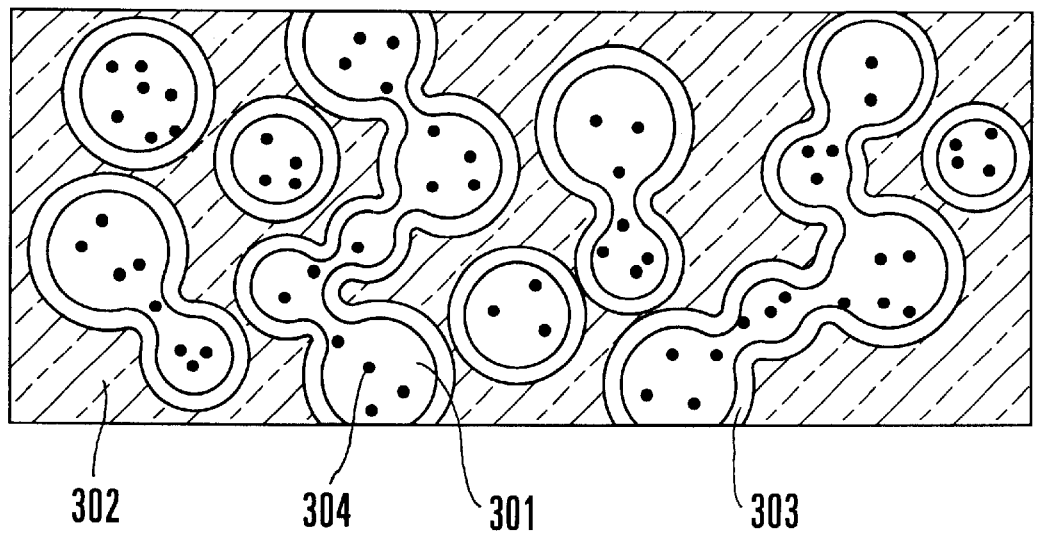
FIGS. 3A to 3C are a view showing the structure of a sensor element of the first embodiment and views for explaining reactions taking place in this element.

As described earlier, the sensor element as a porous body is a transparent matrix absorbent, as shown in FIG. 3A, having a plurality of pores 301 having an average pore-diameter of 20 nm or less. A diazotizing reagent and a coupling reagent are placed together with an acid in the holes 301 of this sensor element (porous body) 302. When this porous body is exposed to air, the pores adsorb water in the air to form a thin water film 303. Consequently, this thin film 303 of an aqueous solution in which the diazotizing reagent, coupling reagent, and acid are dissolved is formed on the inner walls of the pores 301 of the sensor element 302 as this porous body.

Nitrogen dioxide molecules 304 entering the pores 301 encounter these components to cause the following two reactions.

Figure 3B:
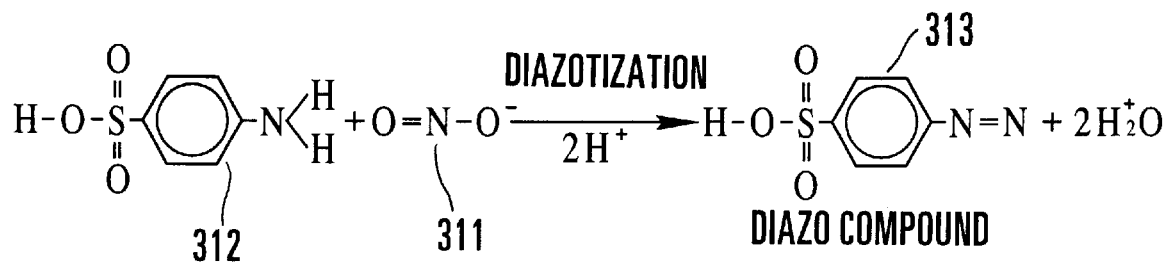

First, as shown in FIG. 3B, sulfanilic acid 312 as the diazotizing reagent reacts with (diazotizes) nitrous ions 311 produced by dissolving nitrogen oxide in water to produce a diazo compound 313.

Figure 3C:
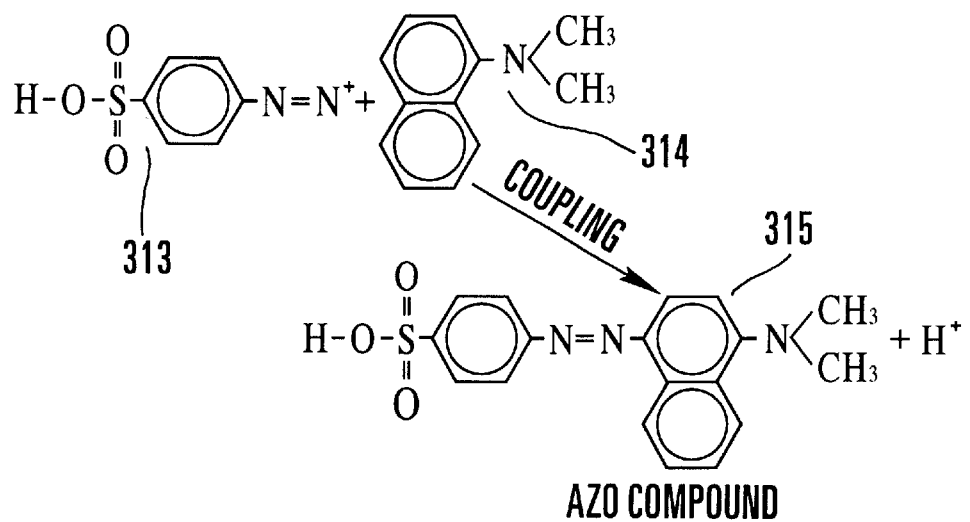

This diazo compound couples with N,N-dimethylnaphthylamine 314 as the coupling reagent to produce an azo compound (coupling compound) 315. Generally, an azo compound (azo dye) has light absorption in a wavelength region of 200 to 2,000 nm. For example, it is known that the azo compound 315 shown in FIG. 3C has an absorption wavelength around 500 to 550 nm. This agrees with the results shown in FIG. 2.

Accordingly, the azo compound can be sensed (determined) by measuring its absorption spectrum by using, e.g., a spectrophotometer (absorptiometer).

Diazotization is a process in which aromatic primary amine ($ArNH_2$) and $NO_2^-$ react with each other to form a diazo compound ($ArN_2^+$) in the presence of two or more equivalents of an acid. For this reason, the above reaction basically occurs only in nitrogen dioxide gas. Since this reaction is $ArNH_2+NO_2^-+2H^+\rightarrow ArN_2^++2H_2O$, it theoretically requires two equivalents of an acid. That is, as described previously, the diazotizing reagent and the coupling reagent together with a necessary amount of an acid must be placed in (carried by) the pores of the porous body. Although the above reaction can also take place in a gas phase, water necessarily exists in an actual environment as mentioned earlier. Essentially, therefore, a thin water film exists in the pores of the sensor element, and the reaction occurs in this aqueous solution.

As described above, nitrogen dioxide gas can be indirectly measured by measuring the light absorption of the azo compound produced as a result of the adsorption of the nitrogen dioxide gas. For example, when the porous body is made from a material which transmits light in the light absorption wavelength region of the azo compound, the light absorption characteristic of the porous body adsorbing nitrogen dioxide gas is measured. Consequently, the adsorbed nitrogen dioxide gas can be sensed.

In this first embodiment as described above, the measurement was done after the sensor element was exposed to air having a nitrogen dioxide concentration of 300 ppb for three hours. As shown in FIG. 2, the absorbance change at 530 nm was as high as about 0.1. This means that high-sensitivity, sub-ppm-level $NO_2$ detection was performed. The measurement could be simply done only by placing the sensor element of this first embodiment in a thin film measurement holder of an absorptiometer. Quantitative determination at ppb level is possible by calculating the relationship between the absorbance difference and the concentration.

As a sensitivity index, an absorbance change at a maximum absorption wavelength per exposure (concentration (ppb)×exposure time (time)) was calculated. In the first embodiment (FIG. 2), the absorbance change when the sensor element was exposed to 300-ppb $NO_2$ gas for three hours was 0.1. Hence, the sensitivity index was $1.1\times10^{-4}$ $ppb^{-1}\cdot hr^{-1}$, i.e., very high sensitivity was obtained.

As the diazotizing reagent, it is also possible to use a compound which is an aromatic compound such as benzene, naphthalene, or biphenyl, or a heterocyclic aromatic compound such as thiophene or thiazole, and which has a primary amino group or an acetamide group. As the coupling reagent, it is also possible to use a compound which is an aromatic compound such as benzene, naphthalene, or biphenyl, or a heterocyclic aromatic compound such as thiophene or thiazole, and which has an amino group (primary to tertiary), an alkoxy group, or a hydroxyl group.

One method of introducing the diazotizing reagent and the coupling reagent into the pores of the porous body is to impregnate the porous body with a solution of the two reagents to introduce them into the pores and dry the resultant material as described above. In addition to this method, it is possible to introduce the two reagents into the pores by evaporating or melting these reagents. In these methods, an acidic environment can be formed by previously introducing an acid into the pores of the porous body. Also, when the porous body is manufactured by a sol-gel method, the two reagents can be introduced into the pores singly or in the form of a mixture with another compound.

As described above, this first embodiment uses the sensor element including the diazotizing reagent and the coupling reagent in the pores of the porous body. Since this increases the area of adsorption of nitrogen dioxide gas to be sensed, the sensitivity and the storage capacity can be increased compared to the conventional methods.

Additionally, the porous body forming the sensor element has a high transmittance in a wavelength region of approximately 400 to 1,000 nm. Therefore, it is possible by measuring the transmittance of the sensor element to measure a change in the absorbance caused by an azo dye produced when the sensor element adsorbs nitrogen dioxide. That is, in this first embodiment, nitrogen dioxide gas adsorbed by the sensor element can be sensed by measuring the absorbance of the sensor element before and after the sensor element is exposed to air to be sensed. This allows easy detection of nitrogen dioxide gas. Also, the measurement of the absorbance is easy because it is only necessary to monitor the change of a single peak during the measurement.

Figure 4:
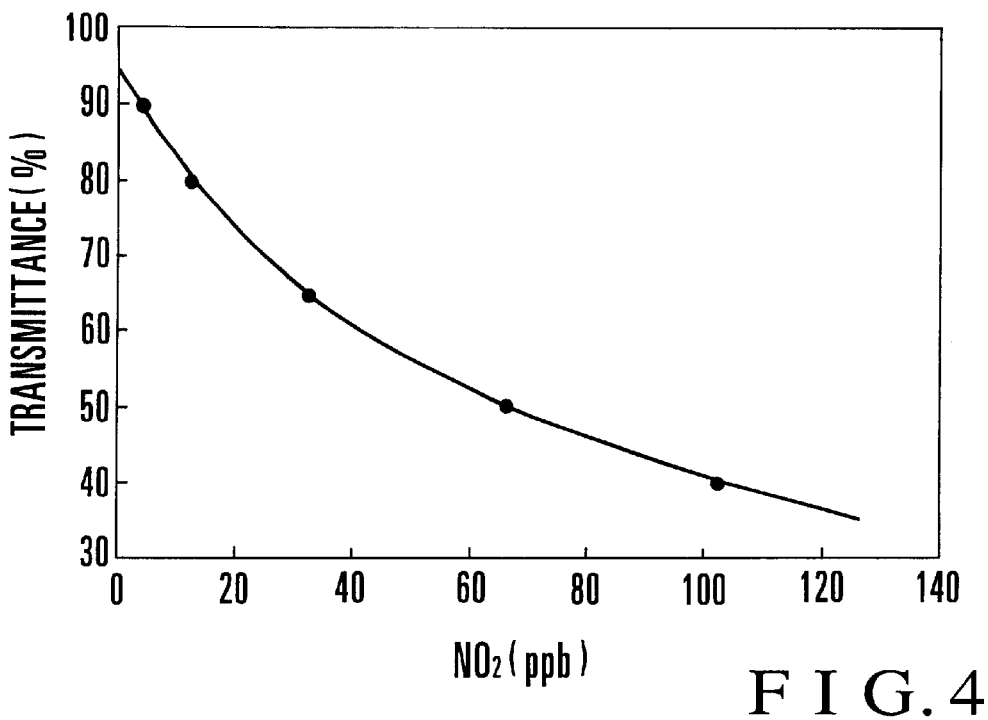
FIG. 4 is a graph showing the transmittance as a function of the nitrogen dioxide concentration in the sensor element of the first embodiment.

As shown in FIG. 4, as the nitrogen dioxide gas concentration in air to be measured increases, the light transmittance at a predetermined wavelength of the sensor element of this first embodiment decreases. This predetermined wavelength is approximately 530 nm.

In this first embodiment as described above, nitrogen dioxide gas can be sensed by an optical change in the small sensor element. Thus, the first embodiment has the effect of very simply and accurately sensing nitrogen dioxide gas.

Figure 5:
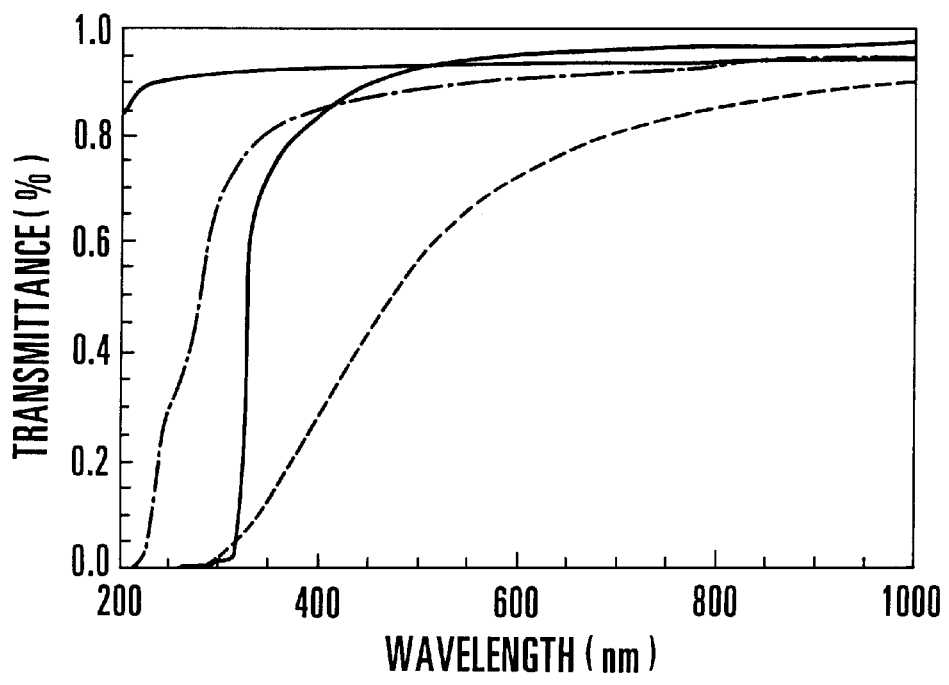
FIG. 5 is a graph showing the relationship between a glass porous body and an optical transmittance.

The porous body forming the sensor element was made from glass (borosilicate glass), and the average pore-diameter was set to 20 nm or less. It was found that light was transmitted in the visible light region (350 to 800 nm) in measuring a transmission spectrum in the UV-visible region (200 to 2,000 nm). When the average pore size was increased, an abrupt transmittance decrease was observed in the visible region. The results are shown in FIG. 5. Referring to FIG. 5, the dotted line indicates the transmittance of quartz; (2) the transmittance of a porous body made from borosilicate glass and having a pore-diameter of 2.5 nm; (3) the transmittance of VYCOR®7930 used in the above first embodiment; and (4) the transmittance of a porous body made from borosilicate glass and having a pore-diameter of 20 nm. The samples indicated by (2) and (2) were manufactured by GELTECH. The thickness of each sample was 1 mm.

Accordingly, the average pore-diameter of the porous body described above is preferably 20 nm or less. Also, a transparent porous body is preferably used in the visible light region of 350 to 800 nm. In the first embodiment, the surface-specific area of the porous body is 200 m$^2$ or more per 1 g.

Second Embodiment

The second embodiment of the present invention will be described below.

First, a method of manufacturing a nitrogen dioxide gas sensor element according to the second embodiment will be described. Sulfanilamide (SFA) as a diazotizing reagent and N,N-dimethylnaphthylamine (DMNA) as a coupling reagent were dissolved in a mixture solution of ethanol to prepare a sensing reagent solution. The concentration of sulfanilamide was 0.02 mol/l. The concentration of N,N-dimethylnaphthylamine was 0.005 mol/l.

Next, a porous body having an average pore-diameter of 4 nm was immersed in this sensing reagent solution. As in the first embodiment, VYCOR®7930 manufactured by Corning Glass Works was used as this porous body. The average pore-size of this VYCOR®7930 was 4 nm. The chip dimensions of the porous body were 8 (mm)×8 (mm) and a thickness of 1 (mm).

This porous body was immersed in the sensing reagent solution for two hours. After the pores of the porous body were impregnated with the sensing reagent solution, the porous body was air-dried. Finally, the porous body was dried by leaving it in a nitrogen gas flow for a half day to manufacture a sensor element of this second embodiment.

FIG. 6 shows the absorption spectra of the sensor element of the second embodiment before and after the element was exposed to air to be measured. The broken line indicates the state before exposure. The solid line indicates the result after the sensor element of the second embodiment was exposed to air containing 300-ppb NO$_2$ for three hours.

As is apparent from FIG. 6, the solid line has only one new absorption peak near 530 nm. It is considered that this absorption near 530 nm was caused by an azo dye produced when N,N-dimethylnaphthylamine coupled with a diazo compound as a diazotized form of sulfanilamide. The absorbance change was as high as about 0.1. It was also found that the sensor element of the second embodiment could perform highly sensitive detection of ppb-level nitrogen dioxide gas.

In the second embodiment (FIG. 6), the sensitivity index was calculated in the same manner as in the first embodiment. The calculated index was $1.3\times10^{-4}$ ppb$^{-1}\cdot$hr$^{-1}$, i.e., very high sensitivity was obtained.

Third Embodiment

The third embodiment of the present invention will be described below.

First, a method of manufacturing a nitrogen dioxide gas sensor element according to the third embodiment will be described. Acetanilide (AA) as a diazotizing reagent and N,N-dimethylnaphthylamine (DMNA) as a coupling reagent were dissolved in a mixture solution of ethanol to prepare a sensing reagent solution. The concentration of acetanilide was 0.02 mol/l. The concentration of N,N-dimethylnaphthylamine was 0.005 mol/l.

Next, a porous body having an average pore-diameter of 4 nm was immersed in this sensing reagent solution. As in the first and second embodiments, VYCOR®7930 manufactured by Corning Glass Works was used as this porous body. The average pore-size of this VYCOR®7930 was 4 nm. The chip dimensions of the porous body were 8 (mm)×8 (mm) and a thickness of 1 (mm).

This porous body was immersed in the sensing reagent solution for two hours. After the pores of the porous body were impregnated with the sensing reagent solution, the porous body was air-dried. Finally, the porous body was dried by leaving it in a nitrogen gas flow for a half day to manufacture a sensor element of this third embodiment.

FIG. 7 shows the absorption spectra of the sensor element of the third embodiment before and after the element was exposed to air to be measured. The broken line indicates the state before exposure. The solid line indicates the result after the sensor element of the third embodiment was exposed to air containing 300-ppb NO$_2$ for three hours.

In this third embodiment, as is apparent from FIG. 7, the solid line has only one new absorption peak near 460 nm. Although this absorbance is about 0.03, highly sensitive ppb-level NO$_2$ detection is well possible.

In the third embodiment (FIG. 7), the sensitivity index was calculated in the same manner as in the first and second embodiments and found to be $3.3\times10^{-5}$ ppb$^{-1}\cdot$hr$^{-1}$.

Fourth Embodiment

The fourth embodiment of the present invention will be described below. This fourth embodiment relates to a nitrogen dioxide gas sensor using the sensor element described above.

Figure 8:
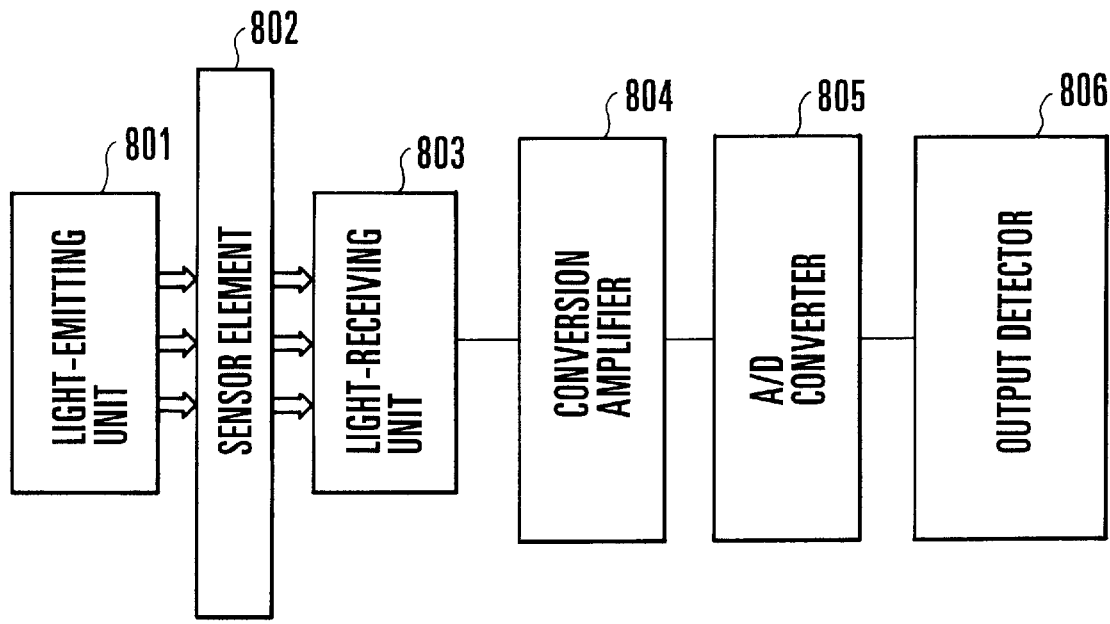
FIG. 8 is a block diagram showing an outline of the arrangement of a nitrogen dioxide gas sensor according to the third embodiment of the present invention.

In this nitrogen dioxide sensor, as shown in FIG. 8, a light-emitting unit 801 which is an LED for emitting light having a predetermined wavelength emits light to a sensor element 802. A light-receiving unit 803 receives the transmitted light. The light-receiving unit 803 photoelectrically converts the received light and outputs a signal current. A conversion amplifier 804 amplifies the output signal current to perform current-voltage conversion. An A/D converter 805 converts the voltage signal into a digital signal. An output detector 806 outputs the digital signal as a detection result.

The sensor element 802 is, e.g., the sensor element of the first embodiment described previously. The light-receiving unit 803 is, e.g., a photodiode. A light-emitting portion of the light-emitting unit 801 and a light-receiving portion of the light-receiving unit 803 oppose each other.

In this fourth embodiment as described above, a nitrogen dioxide gas sensor is realized with a simple arrangement.

Fifth Embodiment

The fifth embodiment of the present invention will be described below. In this embodiment, the above-mentioned nitrogen dioxide gas sensor will be described in more detail. In particular, the arrangements of the light-emitting unit and the light-receiving unit will be described.

Figure 9:
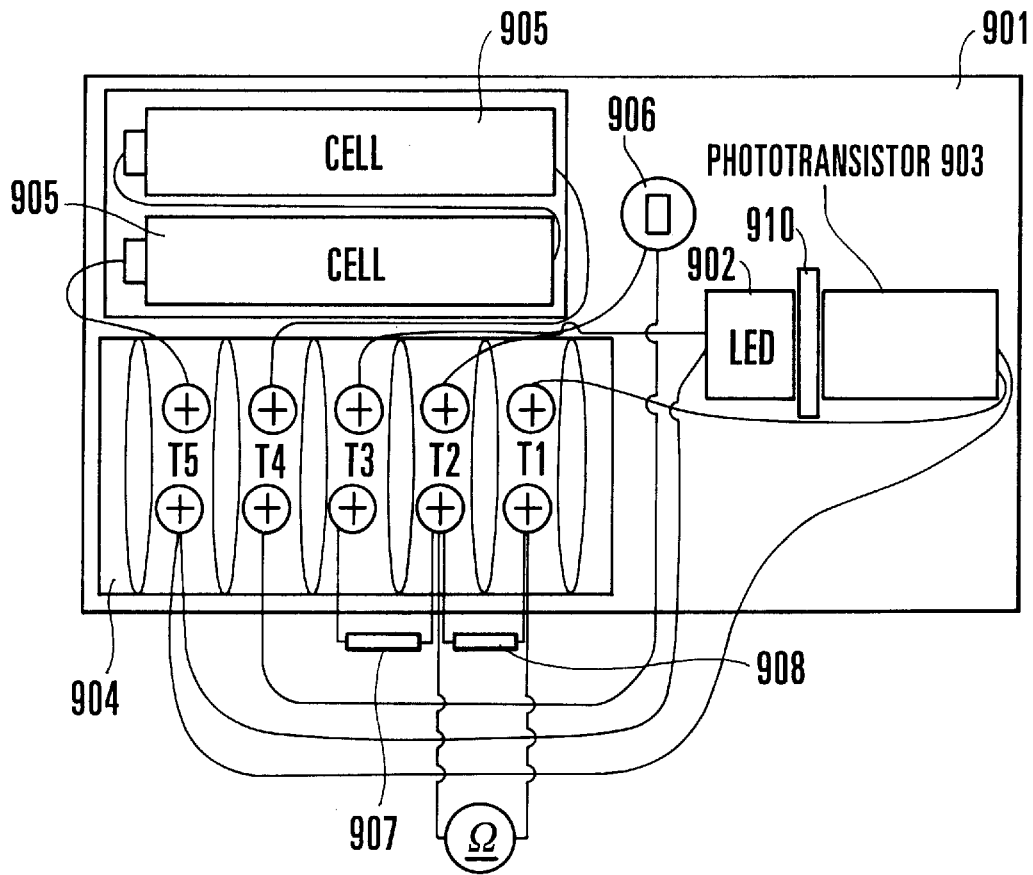
FIG. 9 is a block diagram showing an outline of the arrangement of a nitrogen dioxide gas sensor according to the fourth embodiment of the present invention.

In this fifth embodiment, as shown in FIG. 9, an LED 902 for emitting 550-nm green light and a phototransistor 903 are formed on a substrate 901 about 12 cm×6 cm in size. The light-receiving surface of the phototransistor 903 opposes the light-emitting surface of the LED 902. This phototransistor has optical sensitivity in a wavelength region of 450 to 1,100 nm. Two AA cells 905 connected in series supply power to the LED 902 and the phototransistor 903 via a terminal plate 904. This power supply can be switched on and off by a switch 906. That is, a circuit is assembled by using terminals of the terminal plate 904. A line of the phototransistor 903 is connected to a terminal T1. A line of the switch 906 is connected to a terminal T2. A line of the LED 902 is connected to a terminal T3. A line of the cells 905 is connected to a terminal T4. Lines of the cells 905, the LED 902, and the phototransistor 903 are connected to a terminal T5.

Resistors 907 and 908 are so connected that the phototransistor 903 outputs an order-of-magnitude voltage (V).

A sensor element 910 as described in the first to third embodiments is inserted between the LED 902 and the phototransistor 903. A voltmeter is connected between the terminals T1 and T2 of the terminal plate 904 to measure the voltage. In this manner, the nitrogen dioxide sensor measures nitrogen dioxide gas adsorbed by the sensor element 910.

In this fifth embodiment as described above, an accurate nitrogen dioxide gas sensor can be formed in an area of about 12 cm×6 cm. Additionally, commercially available cells can be used as the power supply, so nitrogen dioxide gas can be sensed more simply.

In the nitrogen dioxide gas sensing method of the present invention as described above, a mixture of a diazotizing reagent which reacts with nitrous ions to produce a diazo compound, a coupling reagent which couples with the diazo compound to produce an azo dye, and an acid is placed in pores of a transparent porous body to prepare a sensor element. The light transmittance of this sensor element is measured to calculate the first transmittance. The sensor element is then exposed to air to be measured for a predetermined time. After that, the light transmittance of the sensor element is measured to calculate the second transmittance. Nitrogen dioxide gas in the air to be measured is sensed in accordance with the difference between the first and second transmittances.

In this method with the above arrangement, when the sensor element is exposed to an atmosphere containing nitrogen dioxide gas, the diazotizing reagent diazotizes nitrous ions produced by nitrogen dioxide adsorbed to pores of the sensor element to produce a diazo compound. The coupling reagent couples with this diazo compound to produce an azo dye. Consequently, the sensor element colors to make a difference between the first and second transmittances. This allows detection of the nitrogen dioxide gas.

Accordingly, it is only necessary to monitor the color change of the sensor element after the sensor element is exposed to the atmosphere to be measured. So, nitrogen dioxide gas can be sensed more simply and accurately than in the conventional methods.

The nitrogen dioxide gas sensor element of the present invention comprises a transparent porous body, a diazotizing reagent placed in pores of the porous body to react with nitrous ions to produce a diazo compound, a coupling reagent placed together with the diazotizing reagent in the pores of the porous body to couple with the diazo compound to produce an azo dye, and an acid placed together with the diazotizing reagent in the pores of the porous body.

When nitrogen dioxide gas enters the pores of the nitrogen dioxide gas sensor element with the above arrangement and is adsorbed to the pores, the diazotizing reagent reacts with nitrous ions produced by the nitrogen dioxide gas to produce a diazo compound. The coupling reagent couples with this diazo compound to produce an azo dye. Consequently, the nitrogen dioxide gas sensor element colors.

Accordingly, nitrogen dioxide gas can be sensed only by monitoring the color change of this nitrogen dioxide gas sensor element. So, nitrogen dioxide gas can be sensed more simply and accurately than in the conventional methods.

The nitrogen dioxide gas sensor of the present invention comprises a light-emitting unit for emitting light, a light-sensing unit having a light-receiving surface opposed to a light-emitting surface of the light-emitting unit to output an electrical signal corresponding to a light amount received by the light-receiving surface, a sensor element inserted between the light-emitting unit and the light-sensing unit, and an electric meter for measuring the state of the output electrical signal from the light-sensing unit. The sensor element comprises a transparent porous body, a diazotizing reagent placed in pores of the porous body to react with nitrous ions to produce a diazo compound, a coupling reagent placed together with the diazotizing reagent in the pores of the porous body to couple with the diazo compound to produce an azo dye, and an acid placed together with the diazotizing reagent in the pores of the porous body.

In the sensor with the above arrangement, when nitrogen dioxide gas enters the pores of the sensor element and is adsorbed to the pores, the diazotizing reagent reacts with nitrous ions produced by the nitrogen dioxide gas to produce a diazo compound. The coupling reagent couples with this diazo compound to produce an azo dye. Consequently, the nitrogen dioxide gas sensor element colors. Meanwhile, the light emitted from the light-emitting unit enters the light-sensing unit via the sensor element. The electric meter measures the color change of the sensor element as a change in the output electrical signal from the light-sensing unit.

Accordingly, this nitrogen dioxide gas sensor can accurately sense nitrogen dioxide gas when placed in an atmosphere to be measured. So, nitrogen dioxide gas can be sensed more simply and accurately than in the conventional methods.

What is claimed is:

1. A nitrogen dioxide gas sensing method comprising:

the first step of preparing a sensor element in which a mixture of a diazotizing reagent which reacts with nitrous ions to produce a diazo compound, a coupling reagent which couples with the diazo compound to produce an azo dye, and an acid is placed in pores of a transparent porous body, wherein the sensor element is capable of detecting nitrogen dioxide gas when the sensor element is in a dry state, and an average pore-diameter of said porous body allows said diazotizing reagent and said coupling reagent to enter the pores and is not more than 20 nm;

the second step of measuring a light transmittance of said sensor element to calculate a first transmittance;

the third step of exposing said sensor element to air top be measured for a predetermined time;

the fourth step of measuring a light transmittance of said sensor element to calculate a second transmittance after the third step; and the fifth step of sensing nitrogen dioxide gas in the air to be measured in accordance with a difference between the first and second transmittances.

2. A method according to claim 1, wherein said diazotizing reagent is a compound selected from the group consisting of an aromatic compound and a heterocyclic aromatic compound, and including a primary amine group or an acetamide group, and said coupling reagent is a compound selected from the group consisting of an aromatic compound and a heterocyclic aromatic compound, and including a primary, secondary, or tertiary amine group, an alkoxy group, or a hydroxyl group.

3. The method of claim 2, wherein said aromatic compound comprises one of benzene, naphthalene and biphenyl.

4. The method of claim 2, wherein said heterocyclic aromatic compound comprises one of thiophene and thiazole.

5. A nitrogen dioxide gas sensor element comprising:

a transparent porous body;

a diazotizing reagent placed in pores of said porous body to react with nitrous ions to produce a diazo compound;

a coupling reagent placed together with said diazotizing reagent in the pores of said porous body to couple with the diazo compound to produce an azo dye; and an acid placed together with said diazotizing reagent in the pores of said porous body, wherein the sensor element is capable of detecting nitrogen dioxide gas when the sensor element is in a dry state, wherein an average pore-diameter of said porous body allows said diazotizing reagent and said coupling reagent to enter the pores and is not more than 20 nm.

6. A method according to claim 5, wherein said diazotizing reagent is a compound selected from the group consisting of an aromatic compound and a heterocyclic aromatic compound, and including a primary amine group or an acetamide group, and said coupling reagent is a compound selected from the group consisting of an aromatic compound and a heterocyclic aromatic compound, and including a primary, secondary, or tertiary amine group, an alkoxy group, or a hydroxyl group.

7. An element according to claim 6, wherein said aromatic compound comprises one of benzene, naphthalene and biphenyl.

8. An element according to claim 6, wherein said heterocyclic aromatic compound comprises one of thiophene and thiazole.

9. A nitrogen dioxide gas sensor comprising:

a light-emitting unit for emitting light;

a light-sensing unit having a light-receiving surface opposed to a light-emitting surface of said light-emitting unit to output an electrical signal corresponding to a light amount received by the light-receiving surface;

a sensor element inserted between said light-emitting unit and said light-sensing unit; and an electrical meter for measuring a state of the output electrical signal from said light-sensing unit, wherein said sensor element comprises a transparent porous body, a diazotizing reagent placed in pores of said porous body to react with nitrous ions to produce a diazo compound, a coupling reagent placed together with said diazotizing reagent in the pores of said porous body to couple with the diazo compound to produce an azo dye, and an acid placed together with said diazotizing reagent in the pores of said porous body, wherein an average pore-diameter of said porous body allows said diazotizing reagent and said coupling reagent to enter the pores and is not more than 20 nm.

10. A sensor according to claim 9, wherein said light-emitting unit comprises a light-emitting diode, said light-sensing unit comprises a phototransistor, and said nitrogen dioxide gas sensor further comprises:

a cell for supplying power to said light-emitting diode and said phototransistor;

a switch for switching on and off the power supply from said cell to said light-emitting diode and said phototransistor;

a voltmeter as an electric meter connected between said phototransistor and said cell;

a terminal plate including terminals for connecting said light-emitting diode, said phototransistor, said cell, said switch, and said voltmeter; and a substrate on which said light-emitting diode, said phototransistor, said cell, said switch, said voltmeter, and said terminal plate are placed.

11. A sensor according to claim 9, wherein said diazotizing reagent is a compound selected from the group consisting of an aromatic compound and a heterocyclic aromatic compound, and including a primary amine group or an acetamide group, and said coupling reagent is a compound selected from the group consisting of an aromatic compound and a heterocyclic aromatic compound, and including a primary, secondary, or tertiary amine group, an alkoxy group, or a hydroxyl group.

12. A sensor according to claim 11, wherein said aromatic compound comprises one of benzene, naphthalene and biphenyl.

13. A sensor according to claim 11, wherein said heterocyclic aromatic compound comprises one of thiophene and thiazole.

* * * * *